United States Patent [19]

Cooper et al.

[11] Patent Number: 5,512,313
[45] Date of Patent: Apr. 30, 1996

[54] ESTERIFIED ALKOXYLATED POLYOL FAT SUBSTITUTES HAVING HIGH PRIMARY ESTER CONTENT

[75] Inventors: Charles F. Cooper, Paoli; Stephen H. Harris, West Chester, both of Pa.

[73] Assignees: ARCO Chemical Technology, L.P., Greenville, Del.; CPC International Inc., Englewood Cliffs, N.J.

[21] Appl. No.: 351,976

[22] Filed: Dec. 8, 1994

Related U.S. Application Data

[62] Division of Ser. No. 114,713, Aug. 31, 1993, Pat. No. 5,399,729.

[51] Int. Cl.$^6$ .................................................. A23D 7/015
[52] U.S. Cl. ...................... 426/611; 426/601; 426/804; 554/149; 554/168
[58] Field of Search ...................................... 426/611, 804

[56] References Cited

U.S. PATENT DOCUMENTS

| | | | |
|---|---|---|---|
| 2,610,125 | 9/1952 | Valko | 99/123 |
| 4,849,242 | 7/1989 | Kershner | 426/601 |
| 4,861,613 | 8/1989 | White et al. | 426/611 |
| 4,983,329 | 1/1991 | Cooper | 426/611 |
| 5,059,443 | 10/1991 | Ennis et al. | 426/611 |
| 5,118,448 | 6/1992 | Cooper | 554/168 |
| 5,135,683 | 8/1992 | Cooper | 554/151 |
| 5,175,323 | 12/1992 | Cooper | 554/164 |
| 5,273,772 | 12/1993 | Cooper | 426/611 |
| 5,308,634 | 5/1994 | Cooper | 426/611 |

FOREIGN PATENT DOCUMENTS

| | | |
|---|---|---|
| 0396406 A | 11/1990 | European Pat. Off. . |
| 0396405 A | 11/1990 | European Pat. Off. . |
| 0415635 A | 3/1991 | European Pat. Off. . |
| 0433016 A | 6/1991 | European Pat. Off. . |
| 0481523 A | 4/1992 | European Pat. Off. . |
| 207070 | 2/1984 | Germany . |
| 53151050 | 6/1980 | Japan . |
| 55-160710 | 12/1980 | Japan . |
| WO92/01386 | 2/1992 | WIPO . |

OTHER PUBLICATIONS

Mieth, G. A., A. Elsner, J. Brucker, A. Weiss and H. Behrens "A Caloric Compounds With Fat–Like Functional Properties", Die Nahrung, vol. 27, No. 9 pp. 853–876, 1993.

Aust, L. G. Mieth, J. Proll, A. Elsner, H. Behrens, W. Gerhardt, J. Brucker, R. Noack, Die Nahrung, vol. 32 No. 1 pp. 49–57, 1988.

*Primary Examiner*—Carolyn Paden
*Attorney, Agent, or Firm*—Stephen D. Harper

[57] ABSTRACT

Reduced calorie food compositions are prepared using fatty acid esterified alkoxylated polyol fat substitutes derived from $C_3$ and higher epoxides and having a high proportion of primary ester linkages. The fat substitutes may be obtained by alkoxylation of a polyol such as glycerin with the epoxide in the presence of a cationic/ring-opening polymerization catalyst, followed by esterification with a fatty acid or a fatty acid equivalent.

6 Claims, No Drawings

ESTERIFIED ALKOXYLATED POLYOL FAT SUBSTITUTES HAVING HIGH PRIMARY ESTER CONTENT

This is a division of application Ser. No. 08/114,713 filed on Aug. 31, 1993 now U.S. Pat. No. 5,399,729.

FIELD OF THE INVENTION

This invention relates to reduced calorie fat substitutes which are fatty acid-esterified alkoxylated polyols wherein a high proportion of the ester linkages present have a primary structure. These fat mimetics are obtainable by cationic ring-opening polymerization of a $C_3$ or higher 1,2-alkylene oxide in the presence of a polyol followed by esterification of the alkoxylated polyol intermediate with a fatty acid or fatty acid equivalent. The esterified alkoxylated polyols are useful as fully functional replacements for edible lipids in the preparation of food compositions having significantly decreased caloric content. The esterified alkoxylated polyol in a preferred embodiment is an esterified propoxylated glycerin having at least 80% primary ester linkages.

BACKGROUND OF THE INVENTION

A wide variety of substances have been proposed for use as fat substitutes in food compositions. The chemical structures of such substances are selected such that they are more resistant to breakdown by the metabolic processes of the human digestive system which normally occur upon ingestion of conventional triglyceride lipids. Because of their increased resistance to digestion and absorption, the number of calories per gram available from these fat substitutes is considerably reduced as compared to common vegetable oils, animal fats, and other lipids. Such substances thus may be utilized in the preparation of reduced calorie food compositions useful in the control of body weight.

U.S. Pat. No. 4,861,613 describes one class of particularly useful fat substitutes wherein a polyol such as glycerin is alkoxylated with an epoxide such as propylene oxide under basic conditions and then esterified with any of a number of fatty acids to form an esterified alkoxylated polyol. These substances have the physical and organoleptic properties of conventional triglyceride lipids, yet are significantly lower in available calories owing to their pronounced resistance towards pancreatic lipase enzymatic hydrolysis. The thermal and oxidative stability of the esterified alkoxylated polyols renders them especially suitable for use in the preparation of reduced calorie food compositions requiring exposure to high temperatures.

Unfortunately, as a consequence of their hydrolytic stability, low digestibility, and lipophilic character the esterified alkoxylated polyols described in U.S. Pat. No. 4,861,613 which are fully liquid at body temperature may tend to cause certain undesirable gastrointestinal side effects when consumed at high levels in the diet. That is, since such esterified alkoxylated polyols are not readily broken down into simpler substances upon ingestion, they retain their oily, fat-like character and pass through the digestive tract in substantially unaltered form. Problems with leakage of the fat substitute through the anal sphincter and separation of the fat substitute as an oil from the excreted fecal matter can occur as a result of the non-digestibility of the fat substitute. Other fat substitutes which are similarly resistant towards digestion are known to produce the same sort of gastrointestinal side effects. Examples include sucrose polyester which is esterified with up to 8 fatty acid groups; see U.S. Pat. Nos. 3,954,976, 4,005,195, 4,005,196, and 5,006,360. Obviously, such problems will greatly limit the maximum level of these substances which can be tolerated in various food compositions, thereby constraining the amount of conventional triglyceride and the number of calories which can be removed from certain foods.

Despite the considerable research performed in the last two decades on synthetically prepared fat substitutes, an understanding of the precise relationship between chemical structure and digestability is still lacking and the field remains a highly uncertain and unpredictable art. The technical literature related to fat substitutes is replete with conflicting observations and findings which cannot easily be reconciled or explained. For example, U.S. Pat. No. 4,861, 613 (White et al.) teaches that a polyol such as glycerin should be reacted (epoxylated) with a quantity of a $C_3$–$C_6$ epoxide sufficient to convert greater than 95% of the primary hydroxyl groups of the polyol to secondary or tertiary hydroxyl groups prior to esterification with a fatty acid in order to obtain a low calorie fat substitute. The non-digestibility of the final esterified alkoxylated polyol was attributed primarily to the presence of secondary and tertiary ester linkages since substances with lower degrees of alkoxylation were found to be susceptible to lipase-catalyzed hydrolysis.

In contrast, U.S. Pat. No. 4,849,242 (Kershner) teaches the preparation of reduced calorie food compositions containing oil-like polymer fatty acid esters having the property of being substantially hydrolyzed during the process of intestinal digestion into a mixture of fatty acids and a non-caloric water-soluble or water-dispersible polymeric alcohol. Fatty acid esters of water-soluble polyoxyalkylenes are said to be particularly useful for this purpose. Kershner teaches that polyoxyethylenes, polyoxypropylenes, and polyoxybutylenes are all equally well-suited for use as the polyoxyalkylene starting material, thus implying that the fatty acid esters of such substances will all be readily hydrolyzed upon ingestion. Thus, no distinction between primary and secondary ester linkages in terms of their susceptibility to enzyme-catalyzed hydrolysis was recognized.

Quite different conclusions were reached in U.S. Pat. Nos. 5,059,443 (Ennis et al.) and 5,077,073 (Ennis et al.), which respectively describe the use of esterified alkoxylated alkyl glycosides and esterified alkoxylated sugars and sugar alcohols as low calorie fat substitutes. The degree and rate of hydrolysis of the ester bonds were found to be quite low for these substances relative to a conventional triglyceride. Moreover, the resistance to hydrolysis was reported to be approximately equally high regardless of whether ethylene oxide or propylene oxide was utilized in the alkoxylation. That is, no significant difference in reactivity was observed between substances with primary ester linkages (derived from ethylene oxide) and substances with secondary ester linkages (derived from propylene oxide).

SUMMARY OF THE INVENTION

We have now found that esterified alkoxylated polyols based on $C_3$–$C_{10}$ 1,2-alkylene oxides, but containing a high proportion of primary ester linkages, are useful as fat substitutes and mimetics. These substances have substantially reduced caloric content relative to natural fats and oils, yet exhibit comparable organoleptic and physical characteristics and are well-tolerated in the intestinal tract. The esterified alkoxylated polyol compositions of this invention thus exhibit a highly desirable balance of properties which heretofore has been quite difficult to attain in practice.

Our invention also provides an esterified alkoxylated polyol composition obtainable by reacting a $C_3$–$C_{10}$ 1,2-alkylene oxide with a polyol in the presence of a cationic ring-opening polymerization catalyst to form an alkoxylated polyol intermediate wherein at least 40% (more preferably, at least 60%; most preferably, at least 80%) of the hydroxyl end-groups of said alkoxylated polyol intermediate are primary hydroxyl end-groups and reacting the alkoxylated polyol intermediate with a fatty acid or fatty acid equivalent. In a preferred embodiment, the 1,2-alkylene oxide is propylene oxide and the polyol is glycerin.

Our invention additionally provides a reduced calorie fat substitute comprising a fatty acid ester of an alkoxylated polyol wherein (a) the polyol has from 2 to 8 hydroxyl groups, (b) from 1 times X to 7 times X oxyalkylene units derived from a $C_3$–$C_{10}$ 1,2-alkylene oxide are attached by ether linkages to the polyol, (c) each alkoxylated polyol is attached through ester linkages to from 0.67 times X to 1.0 times X fatty acid acyl groups, and (d) at least 40% of the ester linkages are primary ester linkages.

Also provided is a reduced calorie fat substitute comprising an esterified alkoxylated polyol having the general formula $$Q + (\text{oxyalkylene})_{\overline{x}} \underset{\underset{R^1}{|}}{C}H - \underset{\underset{R^2}{|}}{C}H - O\overset{\overset{O}{\|}}{C}R^3]_n$$

wherein oxyalkylene is derived from a $C_3$–$C_{10}$ 1,2-alkylene oxide, X is zero or an integer selected such that X times n is from 0 to 56, n is an integer of from 2 to 8, Q is a polyol residue, $R^1$ and $R^2$ are different and are hydrogen or $C_1$–$C_6$ alkyl, with the proviso that $R^1$ and $R^2$ are selected such that at least 40% of $R^2$ groups are hydrogen, and $R^3$ is a $C_5$–$C_{23}$ hydrocarbyl group.

The invention additionally provides a reduced calorie food product comprised of a fat component, wherein said fat component is comprised of the esterified alkoxylated polyol composition described hereinabove. Also provided is a fat component useful for preparing a reduced calorie food product wherein said fat component is comprised of an edible triglyceride such as a natural vegetable or animal fat or oil and the aforementioned esterified alkoxylated polyol composition.

DETAILED DESCRIPTION OF THE INVENTION

The esterified alkoxylated polyols of this invention contain covalently linked polyol residues, oxyalkylene units, and fatty acid acyl groups. The polyol residue corresponds to the generic formula $R(O)_n$ and is derived from a polyol or a polyol equivalent wherein the polyol is a polyhydric alcohol containing two or more hydroxyl groups. R in the foregoing formula thus is an organic moiety such as a hydrocarbyl entity containing at least two carbon atoms, hydrogen, and, optionally, other elements such as oxygen or nitrogen; n is equal to the number of hydroxyl groups on the polyol and is most suitably from 2 to 8. The polyol (which preferably contains primary and/or secondary hydroxyl groups) may be selected from $C_2$–$C_{10}$ aliphatic diols (e.g., ethylene glycol, propylene glycol, 1,3-propanediol, 1,4-butanediol, 1,2-butanediol, 2,3-butanediol, pinacol, 1,2-cyclohexanediol, 1,2-pentanediol, 1,4-pentanediol, 1,5-pentanediol, 2,4-pentanediol, 3,3-dimethyl-1, 2-butanediol, 2-ethyl-2-methyl-1, 2-propanediol, 1,2-hexanediol, 1,5-hexanediol, 1,6-hexanediol, 1,7-heptanediol, 2-ethyl-2-(hydroxymethyl)-1, 3-propanediol, $C_3$–$C_{12}$ aliphatic triols (e.g., glycerol, 1,2,4-butane triol, 2,3,4-pentane triol, 2-ethyl-2-(hydroxymethyl)-1,3-propane triol (trimethylol propane), 1,1,1-tris(hydroxymethyl)ethane, 1,2,6-trihydroxyhexane, 1,2,3-heptanetriol, and the like), pentaerythritol, sugar alcohols [including those compounds corresponding to the formula $HOCH_2(CHOH)_nCH_2OH$ wherein n is 2 to 6 such as erythritol, xylitol, sorbitol, arabitol, mannitol, and the like], monosaccharides (e.g., erythrose, threose, ribose, arabinose, xylose, lyxose, allose, altrose, glucose, mannose, gulose, idose, galactose, fructose, galactose, and the like), disaccharides (e.g., sucrose, lactose, maltose) and alkyl glycosides (e.g., methyl glycosides, ethyl glycosides, propyl glycosides, and other glycoside molecules wherein the alkyl glycoside is an acetal formed by interaction of a $C_1$–$C_{20}$ alcohol with a carbonyl group of a mono- or disaccharide such as glucose). Also suitable for use as the polyol are relatively low molecular weight alkoxylated adducts of the aforementioned $C_2$–$C_{10}$ aliphatic diols, $C_3$–$C_{12}$ aliphatic triols, pentaerythritol, sugar alcohols, monosaccharides, disaccharides, and alkyl glycosides, especially ethoxylated, propoxylated, and butoxylated adducts having number average molecular weights of from 106 to 500. Examples of such adducts (which may be prepared by base-catalyzed alkoxylation of a suitable polyol) include, but are not limited to, propoxylated glycerin, diethylene glycol, tripropylene glycol, propoxylated sucrose, ethoxylated trimethylol propane, and the like. Also suitable for use as the polyol are hydroxy-containing substances such as tetrahydrofuran oligomers, oxetane oligomers, glycerol oligomers, alkoxylated glycerol oligomers, and the like.

In a preferred embodiment, the polyol is glycerin so as to provide a glyceryl residue having the structure

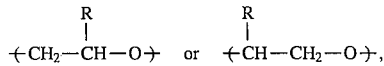

in the esterified alkoxylated polyol (i.e., R= $C_3H_5$ and n=3 in the foregoing formula). Glycerin may be readily and economically obtained by hydrolytic splitting of a natural triglyceride. The fatty acids obtained in such a splitting operation may be utilized in the esterification of the alkoxylated polyol intermediate.

The oxyalkylene units are generally interspersed between the polyol residue and the acyl groups and have the structure $$+CH_2-\underset{\underset{R}{|}}{C}H-O+ \quad \text{or} \quad +\underset{\underset{R}{|}}{C}H-CH_2-O+,$$

wherein R is preferably a $C_1$–$C_6$ alkyl group such as methyl, ethyl, n-propyl, iso-propyl, cyclohexyl, and the like. Typically, more than one oxyalkylene unit may be present between an oxygen of an individual polyol residue and an acyl group such that a polyoxyalkylene sequence is created. However, a single "branch" or "arm" of a esterified alkoxylated polyol compound may contain only one oxyalkylene unit. Some portion of the acyl groups may be attached directly to the polyol residue, without an intervening oxyalkylene unit, although it is preferred that less than 25% of the acyl groups be attached in this manner. In a preferred embodiment, the number of oxyalkylene units per hydroxyl group in the polyol is from 1 to 7 (more preferably, from 1.5 to 5). Thus, where the polyol is a triol such as glycerin, the preferred number of oxyalkylene units per equivalent of triol in the esterified alkoxylated polyol is from 3 to 21.

The oxyalkylene units are obtainable by ring-opening of a $C_3$ or higher 1,2-alkylene oxide under cationic conditions such that ring-opening at the 2 position to yield a primary hydroxyl terminus is favored over ring-opening at the 1 position (which would produce a secondary or tertiary hydroxyl terminus). The 1,2-alkylene oxide may be any organic compound containing a three-membered cyclic ether (oxirane) group in a terminal position and advantageously is a $C_3$–$C_{10}$ aliphatic epoxide. Illustrative epoxides which may be utilized include, but are not limited to, propylene oxide, 1,2-butylene oxide, isobutylene oxide, 1-pentene oxide, vinyl cyclohexane oxide, 1-octene oxide, styrene oxide, allyl glycidyl ether, phenyl glycidyl ether, ethyl glycidyl ether, epichlorohydrin, and the like and mixtures thereof. Due to its low cost, high reactivity, and favorable influence on esterified alkoxylated polyol fat substitute properties, the use of propylene oxide as the sole or predominate (i.e., over 50 mole %) 1,2-alkylene oxide is preferred. Preferably, the compositions of this invention are prepared without the use of ethylene oxide.

To attain the esterified alkoxylated polyol compositions of the invention, it is critical to carry out the ring-opening of the 1,2-alkylene oxide which will comprise the oxyalkylene unit adjacent to the acyl group in such a manner that at least 40% (more preferably, at least 60%, most preferably, at least 80%) of the ester linkages present will be primary in structure (i.e.,

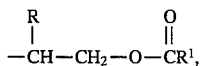

wherein R is a $C_1$–$C_6$ alkyl group and $R^1$ is preferably a $C_5$–$C_{23}$ hydrocarbyl group). "Primary ester linkage" in this context means that the carbon atom attached to the oxygen adjacent to carbonyl bears two hydrogen atoms; in a secondary ester linkage, the analogous carbon atom bears only one hydrogen atom. These structural features distinguish the instant compositions from the related prior art fat substitutes disclosed in U.S. Pat. Nos. 5,059,443 and 5,077,073, which rely on the use of ethylene oxide to provide primary ester linkages, and those disclosed in U.S. Pat. No. 4,861,613, which contain a high proportion of secondary or tertiary ester linkages resulting from the use of higher epoxides such as propylene oxide under base-catalyzed alkoxylation conditions.

The fatty acid acyl groups in the esterified alkoxylated polyol are derived from $C_6$–$C_{24}$ fatty acids or equivalents thereof. These fatty acids may be linear or branched in structure and may be saturated, mono-unsaturated, or polyunsaturated (more than one carbon-carbon double bond). Preferably, monocarboxylic acids (i.e., fatty acids containing only one carboxylic acid functionality) are employed. Such fatty acids and their equivalents (e.g., fatty acid esters, fatty acid halides, fatty acid anhydrides) are readily available at low cost from natural sources such as edible triglycerides. Specific illustrative fatty acids suitable for use include, but are not limited to, eicosanoic (arachidic) acid, heneicosanoic acid, docosanoic (behenic) acid, tricosanoic acid, tetracosanoic (lignoceric) acid, caprylic acid, pelargonic acid, capric acid, caproic acid, lauric acid, palmitic acid, stearic acid, oleic acid, cetoleic acid, myristic acid, palmitoleic acid, gadoleic acid, erucic acid, rincinoleic acid, linoleic acid, linolenic acid, myristoleic acid, eleostearic acid, arachidonic acid, or mixtures or hydrogenated derivatives of these acids.

Mixtures of esterified alkoxylated polyols having structures of the general type described hereinabove may also be employed as useful reduced calorie fat substitutes in the preparation of food compositions.

In an especially desirable embodiment of the invention, the esterified alkoxylated polyol has the general formula

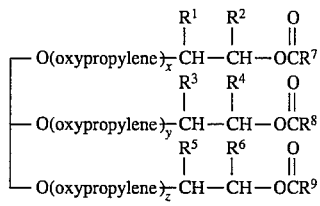

wherein oxypropylene is

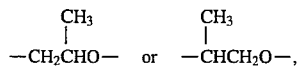

x, y, and z are the same or different and are equal to zero or an integer independently selected such that the sum of x+y+z is from 0 to 12, $R^1$ and $R^2$ are different and are hydrogen or methyl, $R^3$ and $R^4$ are different and are hydrogen or methyl, $R^5$ and $R^6$ are different and are hydrogen or methyl, with the proviso that $R^2$, $R^4$, and $R^6$ are selected such that at least two of said R groups are hydrogen, and $R^7$, $R^8$, and $R^9$ are the same or different and are $C_7$–$C_{23}$ hydrocarbyl (linear or branched; saturated, mono-unsaturated, or polyunsaturated aliphatic).

The esterified alkoxylated polyols, despite containing at least 40% primary ester linkages, typically display normalized hydrolysis rates of less than 20% as compared to an olive oil (conventional triglyceride) standard using porcine pancreatic lipase as catalyst. Normalized hydrolysis rates of less than 10% relative to olive oil are also readily attainable. This result was quite unexpected in view of the teaching of U.S. Pat. No. 4,861,613 that hydrolysis resistance of this magnitude in an esterified alkoxylated polyol is only achieved when the primary ester linkage content is less than 5%.

The pronounced resistance to lipase-catalyzed hydrolysis exhibited by the esterified alkoxylated polyols of this invention indicates that such substances will have desirably low caloric availability when ingested as part of a food composition. At the same time, however, sufficient hydrolysis or other metabolic breakdown takes place (particularly by the time the food reaches the lower intestinal tract) that problems with anal oil leakage are expected to be considerably alleviated as compared to other known fat substitutes. This makes possible the use of esterified alkoxylated polyols which are fully or partially liquid at body temperature, thereby avoiding the need to use a partially or fully solid fat mimetic of the type described in U.S. Ser. No. 07/886,538, filed May 20, 1992. The fat substitutes of this invention may consequently be readily utilized in a wide variety of foods, including those which conventionally are formulated using liquid cooking oils.

In a preferred embodiment of the invention, the esterified alkoxylated polyol has a normalized hydrolysis rate which is from 0.5 to 20% (more preferably, from 1 to 10%) of the rate exhibited by olive oil. The proportion of primary ester linkages, degree of alkoxylation, fatty acid composition and other characteristics of the esterified alkoxylated polyol may be controlled so as to vary the normalized hydrolysis rate and available caloric content as desired. Without wishing to be bound by theory, it is believed that partial hydrolysis of the esterified alkoxylated polyol may generate species that tend to emulsify the undigested portion of the esterified alkoxylated polyol, thereby minimizing separation of the fat substitute from excreted fecal matter.

In the prior art, esterified alkoxylated polyols have been typically prepared by the base-catalyzed reaction of the polyol with epoxide followed by esterification of the alkoxylated polyol intermediate with a fatty acid or fatty acid equivalent such as an alkyl ester, halide, or anhydride of a fatty acid. However, such methods are unsuitable for the synthesis of the esterified alkoxylated polyols of this invention, which are distinguishable from analogous known compounds by their high primary ester content. A $C_3$ or higher 1,2-alkylene oxide ring-opens under basic conditions at least about 98% of the time so as to form a secondary alcohol (see, for example, Gibson et al., *J. Appl. Polymer Sci.* 14, 1059–1067 (1960)). It has now been found, however, that this problem may be overcome through the use of a cationic ring-opening polymerization catalyst (sometimes also referred to as an initiator). Such catalysts include, but are not limited to, inorganic protonic acids [e.g., $HClO_4$, $HSO_3F$, $HSO_3Cl$, $H_2SnCl_6$, $HIO_3$, $HSbCl_6$, $HFeCl_4$, fuming sulfuric acid], bis (fluorinated aliphatic sulfonyl) alkanes [e.g., bis (trifluoromethyl sulfonyl) methane, bis (difluorochloromethyl sulfonyl)methane], fluorinated acids of formula $HXF_n$ where X is boron, phosphorus, arsenic, or antimony and n is 3 where X is boron and 5 where X is phosphorus, antimony, or arsenic [e.g., $HBF_4$, $HPF_6$, $HSbF_6$, $HAsF_6$], Lewis base complexes (e.g., etherates) of such fluorinated acids, trialkyloxonium salts (e.g., $[(C_2H_5)_3O]BF_4$), fluorinated Lewis acids of formula $XF_{n-1}$ where X and n have the same meanings as in the fluorinated acids mentioned hereinabove [e.g., $BF_3$, $PF_5$, $SbF_5$, $AsF_5$], Lewis base complexes (e.g., etherates) of such fluorinated Lewis acids, heteropolyacids [e.g., phosphomolybodic acid, phosphotungstic acid, silicomolybdic acid, silicotungstic acid, or other inorganic polyacids formed from two or more metallic elements where the polycomponent is preferably Mo, V, or W and the hetero component is at least one of the elements Si, P, Ti, Ge, Ar, Zr, Sn, Ce, Cr, Co, Ni, Fe, or Cu, especially those which contain Mo or W together with P or Si], salts of said heteropolyacids [especially the metallic salts, ammonium salts, and amine salts described in Japanese Kokai No. 61-268,727], bleaching earths [e.g., acid-treated montmorillonite clays, including synthetically-prepared or naturally-occurring clay minerals which have been contacted or washed with a strong acid and which use aluminum silicates or aluminum magnesium silicates], and mixtures thereof. The catalyst may be heterogeneous or homogeneous in character, but preferably is a heterogeneous (insoluble) type such as a bleaching earth which may be readily recovered and recycled. In another preferred embodiment, however, the catalyst is boron trifluoride etherate; this catalyst has been found to provide an alkoxylated polyol having a surprisingly high primary hydroxyl content, especially when the polyol is glycerin.

The optimum amount of catalyst to be utilized will vary depending upon the activity of the particular catalyst selected for use, as well as other factors such as temperature and the reactivity of the $C_3$–$C_{10}$ 1,2-alkylene oxide, but should be a concentration sufficient to effect substantial conversion of the 1,2-alkylene oxide with minimal side reactions within a practicably short period of time. Such optimization procedures will be well-known to those familiar with the art of cationic polymerization of cyclic ether monomers. For example, advantageous results are generally achieved when the catalyst is a bleaching earth if the bleaching earth is present in an amount of from 0.1 to 10 weight percent based on the total combined weight of $C_3$–$C_{10}$ 1,2-alkylene oxide and polyol. When a Lewis base complex of a fluorinated acid corresponding to the formula $XF_{n-1}$ such as boron trifluoride etherate is used, the preferred catalyst concentration is in the range of 0.01 to 1 weight percent. If a heteropolyacid is selected as the catalyst, an amount within the range of 0.01 to 5 weight percent will generally be appropriate.

To minimize the formation of undesired by-products such as cyclic oligomers from the 1,2-alkylene oxide, it is usually preferred to first combine the cationic ring-opening polymerization catalyst and the polyol and to subsequently add the 1,2-alkylene oxide slowly in a continuous or semi-continuous manner to the catalyst/polyol mixture. The use of activated monomer techniques such as those described in PCT WO 90/1592 (published Dec. 12, 1990), Wojtania st al., *Makromol. Chem., Macromol. Symp.* 6, 201–206 (1986), and Bednarek et al., Makromol Chem., Suppl. 15 49–60 (1989) may also be advantageous. While the temperature at which the components of the reaction mixture are contacted is not critical, it should be sufficiently high so as to accomplish a relatively rapid rate of reaction, but not so high that impurity formation or degradation is favored over the desired ring-opening addition of the 1,2-alkylene oxide onto the hydroxyl groups of the polyol in a manner such that a high primary hydroxyl content is attained. Although reaction temperatures of from –60° C. to 150° C. may be utilized, the temperature range generally preferred, depending upon the catalyst and 1,2-alkylene oxide selected for use, is from –20° C. to 120° C. The reaction time required to achieve the desired degree of alkoxylation of the polyol will vary as a consequence of the several interrelated variables affecting the rate of reaction. For the most part, however, reaction times of from 0.25 to 48 hours (including 1,2-alkylene oxide addition time) will be sufficient. Sufficient 1,2-alkylene oxide is used relative to the quantity of polyol so as to attain the ratio of oxyalkylene units to polyol desired in the alkoxylated polyol intermediate. In a preferred embodiment of this invention, from 1 to 7 equivalents of 1,2-alkylene oxide is reacted with each equivalent of hydroxyl groups in the polyol. Where the polyol is a triol such as glycerin, for example, from 3 to 21 equivalents of 1,2-alkylene oxide is preferably reacted with each equivalent of triol. Under certain circumstances, it may be desirable to utilize an excess of 1,2-alkylene oxide relative to the amount desired for incorporation into the alkoxylated polyol and to carry out only partial conversion of the 1,2-alkylene oxide. The unreacted 1,2-alkylene oxide may be thereafter recovered from the alkoxylated polyol and recycled in further alkoxylation reactions.

In order to dissolve the reaction components or to permit more efficient heat removal or mixing, it may be desirable to have an inert solvent present. Non-protic solvents such as aromatic hydrocarbons, aliphatic hydrocarbons, and halogenated hydrocarbons are generally suitable for this purpose. The reaction components may be selected such that no solvent is needed, however, which will simplify the separation and recovery steps thereafter required.

After the desired degree of 1,2-alkylene oxide conversion has taken place, the alkoxylation reaction may be stopped by removing or neutralizing the cationic polymerization catalyst. Alternatively, however, the catalyst may be left in the alkoxylated polyol so that it may additionally function as a catalyst for the subsequent esterification reaction.

The alkoxylated polyol intermediate may be esterified by reacting with a fatty acid entity capable of incorporating fatty acid acyl groups onto the alkoxylated polyol selected from the group consisting of fatty acids, fatty acid esters, fatty acid anhydrides and fatty acid halides. The esterification will yield an esterified alkoxylated polyol having acyl groups bonded to the alkoxylated polyol through ester linkages, a high proportion of which (at least 40%) are primary ester linkages.

The fatty acid compound may preferably be a fatty acid or fatty acid ester having the general structure

RCOR' wherein R is a $C_7$–$C_{23}$ olefinic (mono-unsaturated or polyunsaturated) or paraffinic (saturated) hydrocarbon radical and R' is hydrogen or a $C_1$–$C_6$ hydrocarbon radical. Examples of suitable fatty acids include, but are not limited to, caprylic, capric, lauric, myristic, myristoleic, stearic, isostearic, palmitic, palmitoleic, rincinoleic, linoleic, linolenic, elaeostearic, arachidic, arachidonic, behenic, erucic, oleic, and heptadecanoic acid. Short chain, medium chain, and long chain fatty acids, as well as any and all combinations thereof are all suitable for use. The fatty acids may be derived synthetically or from natural sources such as triglyceride lipids. Exemplary fatty acid esters include the methyl, ethyl, propyl, and isopropyl esters of the foregoing fatty acids. Mixtures of fatty acid entities, such as the mixtures of fatty acids typically obtained by hydrolysis (splitting) of a triglyceride such as corn oil or soybean oil, may be used.

Fatty acid halides which may be used can have the general structure

RCX wherein R is a $C_7$–$C_{23}$ olefinic or paraffinic hydrocarbon radical and X is halide, preferably chloride or bromide. Fatty acid anhydrides suitable for use may correspond to the general formula

RCOCR' wherein R and R' are the same or different and are independently selected from $C_7$–$C_{23}$ olefinic (monounsaturated, polyunsaturated) or paraffinic hydrocarbon radicals.

The alkoxylated polyol intermediate and the fatty acid entity are reacted for a time and at a temperature sufficient to accomplish substantially complete (i.e., greater than 67%, more preferably, greater than 90%) esterification of the hydroxyl groups of the alkoxylated polyol. The optimum reaction conditions will vary somewhat depending upon the particular type of fatty acid entity used. If a fatty acid or fatty acid ester is utilized, the reaction temperature is preferably from about 100° C. to 350° C.; reaction times of from about 0.5 to 48 hours are generally sufficient to accomplish substantially complete esterification of the hydroxyl groups. A co-product having the structure HOR' (i.e., water or an alcohol) will be generated as the esterification proceeds. To drive the reaction to completion, it is desirable to remove the co-product from the reaction mixture as it forms by a suitable method such as distillation or vacuum stripping. A catalyst may be employed if desired to shorten the reaction time required. If the fatty acid entity is a free fatty acid, the catalyst is preferably an acidic catalyst. As discussed hereinabove, the cationic ring-opening polymerization catalyst employed in preparation of the alkoxylated polyol may also be used to catalyze the esterification step. Other suitable acidic esterification catalysts include sulphonic acids, sulfuric acid, phosphorus pentoxide, hypophosphonic acid, cationic exchange resins, tin chloride, titanium alkoxide, aluminum or nickel alloys, zinc chloride or the like. If a fatty acid ester is used, an acidic or basic catalyst may be present during esterification. When the fatty acid compound is a fatty acid halide, somewhat lower reaction temperatures (e.g., about 25° C. to 125° C.) are sufficient, particularly if a tertiary amine such as triethylamine is additionally present to take up the hydrogen halide generated during the esterification reaction. Reaction times of from about 1 to 48 hours are typically sufficient. Similar reaction conditions may be utilized when the fatty acid entity is a fatty acid anhydride such as lauric anhydride or oleic anhydride.

To accomplish substantially complete esterification of the alkoxylated polyol intermediate, at least about 1 (more preferably, at least about 1.1) equivalent of the fatty acid entity per equivalent of hydroxyl groups in the alkoxylated polyol is used. For reasons of economy, it is preferred to utilize not more than about 3 equivalents of fatty acid entity per equivalent of hydroxyl groups.

Where the fatty acid entity is a fatty acid and no added acidic catalyst is present, the esterification preferably is self-catalyzed using a slight to moderate excess of fatty acid. In this embodiment, the number of moles of fatty acid is preferably from 1.05×n×moles of polyol to 1.40×n×moles of polyol (where n is an integer of from 2 to 8 and is equal to number of hydroxyl groups on the polyol).

The fatty acid is preferably a $C_6$–$C_{24}$ saturated or unsaturated (including polyunsaturated and cis or trans) fatty acid and may be either linear or branched in structure. Such substances may be readily obtained from natural sources by the well-known hydrolytic splitting (hydrolysis) of the triglycerides from edible fats and oils. The fat or oil may be fully or partially hydrogenated prior to splitting. Alternatively, the fatty acids may be hydrogenated after hydrolysis or after incorporation into the esterified alkoxylated polyol. A single fatty acid or a mixture of different fatty acids may be used. Illustrative examples of suitable fatty acids include, but are not limited to, caprylic acid, caproic acid, capric acid, pelargonic acid, lauric acid, myristic acid, palmitic acid, palmitoleic acid, stearic acid, oleic acid, elaidic acid, linoleic acid, linolenic acid, arachidic acid, gadoleic acid, behenic acid, lignoceric acid, and the like.

In order to achieve a relatively rapid rate of esterification while avoiding problems with dehydration of the alkoxylated polyol, oxidation of the reaction components, or other undesired side reactions, it is generally desirable to carry out the esterification using fatty acids at a temperature of from 150° C. to 300° C. (more preferably, 180° C. to 275° C.) and in the substantial absence of molecular oxygen. The esterification rate can be suitably enhanced by providing a means for removing or binding the water generated during esterification so as to drive the reaction to completion or near completion. For example, a reduced pressure of from about 0.01 mm up to atmospheric (more preferably, from 1 to 50 mm) may be utilized to take the water overhead. An inert gas such as nitrogen, helium, an aliphatic hydrocarbon, carbon dioxide or the like may be sparged or passed through the reaction mixture in order to remove the water as it is formed. Azeotropic distillation of the water with a suitable azeotropic agent (entrainer) such as an aliphatic or aromatic hydrocarbon will also be effective for this purpose. The use of molecular sieves or other water absorbing or reactive substances may also be helpful in reducing the reaction time required to achieve a high degree of hydroxy group conversion. The conditions for water removal are selected such that a minimum amount of fatty acid is taken overhead. Typically, reaction times of from 0.5 to 48 hours will be sufficient to provide substantially complete esterification.

Once the desired degree of esterification has been accomplished, any residual unreacted fatty acid should be removed from the esterified alkoxylated polyol so as to lower the acidity to a level which will be acceptable in food applications. Suitable methods include vacuum steam stripping (distillation) at an elevated temperature (as described, for example, in U.S. Pat. No. 4,983,329), alkali neutralization to precipitate fatty acid salts which may then be removed by filtration, extraction (with methanol, for example), and dilution with a solvent such as hexane in which the desired product is soluble and the fatty acid is insoluble followed by filtration. Unreacted or excess fatty acid ester, fatty acid anhydride, or fatty acid halide may also be removed from the esterified alkoxylated polyol by any suitable method.

The reduced calorie fat substitute produced by the process of this invention can be additionally purified or treated so as to render it more suitable for use in food compositions using any of the techniques known in the art for refining natural vegetable or animal lipids. Such techniques include, but are not limited to, degumming, bleaching, filtration, deodorization, hydrogenation, dewaxing, and the like. Various additives such as stabilizers, anti-oxidants (e.g., tocopherols, hindered phenols such as BHT, hydroquinones such as TBHQ), vitamins (e.g., fat-soluble vitamins such as vitamin A, D, E, and K) and so forth can also be incorporated into the esterified alkoxylated polyol.

It should be understood that by the nature of the reactions described hereinabove in the preparation of the esterified alkoxylated polyols, the compositions obtained will generally be mixtures of individual compounds which have a range of molecular weight and which may contain structural isomers. Such mixtures may be adequately characterized and distinguished from prior art compositions by measurement of average values (for example, the proportion of primary ester linkages) by conventional analytical techniques.

The esterified alkoxylated polyols of this invention may be used as partial or total (100%) replacements for conventional lipids in any edible fat-containing food composition. The amount of the fat mimetic employed is sufficient to effectively reduce the available calories of the food composition as compared to a food composition prepared using an equivalent amount (weight or volume) of a conventional fully digestible triglyceride lipid alone. Preferably, at least about 10 percent (more preferably, at least about 25 percent by weight) of the total fat-like component of the food composition is comprised of the esterified alkoxylated polyol.

The triglyceride lipid admixed with the esterified propoxylated glycerin composition may be any of the known edible fatty acid triglycerides available from natural or synthetic sources. These edible fatty acid triglycerides include, but are not limited to, fats and oils such as tallow, soybean oil, cottonseed oil, coconut oil, palm kernal oil, corn oil, fish oil, lard, butterfat, olive oil, palm oil, peanut oil, safflower seed oil, cocoa butter, sesame seed oil, rapeseed oil, sunflower seed oil, as well as fully or partially hydrogenated derivatives and mixtures of these triglycerides. While the esterified alkoxylated polyol composition may be combined in any proportion with the triglyceride lipid, weight ratios of from 5:95 to 95:5 are particularly advantageous. The triglyceride lipid may be selected so as to impart a desirable caloric content, flavor, aroma, mouth feel, thermal stability, viscosity, rheology (Newtonian or non-Newtonian) or other property to the blend and to the final food composition.

The physical, organoleptic, and physiological properties and characteristics of the esterified alkoxylated polyols of this invention may be controlled as desired by varying the identities and relative proportions of the polyol, 1,2-alkylene oxide, and fatty acids incorporated therein. The composition of the alkoxylated polyols may thus be readily altered so as to render the fat substitute completely liquid, completely solid, or partially liquid and partially solid at room temperature (i.e., the solid fat index may range from 0 to 100%).

Certain relatively high-melting esterified alkoxylated polyols within the scope of this invention may tend to have a waxy or gritty mouthfeel as a consequence of their high solids content at room or body temperature. To eliminate or minimize any such unpleasant organoleptic properties, the fat substitutes are preferably combined with one or more liquid triglyceride lipids. The lipid may be any of the fatty acid triglycerides discussed hereinabove provided it has a complete melting point of 37° C. (body temperature) or below (more preferably, a complete melting point of 25° C. or below). The esterified alkoxylated polyol is advantageously dispersed in the form of fine particles in a matrix of the liquid triglyceride lipid. Preferably, the particles have an average size of 25 microns or less (more preferably, 10 microns or less). The weight ratio of liquid triglyceride lipid to esterified alkoxylated polyol is more desirably from about 0.5:1 to about 10:1 (more preferably from about 1.5:1 to about 4:1). To obtain dispersions of this type, the esterified alkoxylated polyol and liquid triglyceride lipid may be combined in slurry form and the resulting slurry subjected to milling. The temperature during the milling operation, which reduces the particle size of the esterified alkoxylated polyol to the desired level, should be maintained below (preferably, at least 15° F. below) the complete melting point of the esterified alkoxylated polyol (the minimum temperature at which it has a solid-fat index of 0).

The fat substitute of this invention can replace, in full or in part, a triglyceride lipid in a cooking oil, frying oil, salad oil, or shortening, for example. Additional uses include combining the esterified alkoxylated polyol with other foodstuff ingredients to form food compositions such as frozen desserts (e.g., sherbert, ice cream, frozen yogurt, milk shakes), baked goods (cakes, doughnuts, muffins, brownies, breads, pies, rolls, pastries, cookies, biscuits, crackers), nut butters (peanut butter), dairy products (margarine, sour cream, coffee lighteners, cheese, cheese spreads, flavored dips, filled cream, filled milk), mayonnaise, salad dressing, savory snacks (potato chips, corn chips, cheese puffs, pretzels), fried foods (fried poultry, fritters, fried pies, fried vegetables such as french fried potatoes, fried fish), reformed and comminuted meats (lunch meats, sausage, hot dogs, hamburger), pet foods, meat and egg substitutes or extenders, whipped toppings, gravies and other sauces, frostings, fillings, icings, cocoa butter replacements or blends, candies and confectionaries (especially those normally containing fatty ingredients such as chocolate or peanut butter), soups, and dry baking mixes (for muffins, cakes, pancakes, waffles, brownies, and the like). Owing to the fat-like properties and stability of the esterified alkoxylated polyols, minimum reformulation of standard food compositions will generally be required. The viscosity, melting profile, yield point, hardness, thixotropic area, liquid/solid stability, solid fat index, rheology, plasticity, and other physical properties of the esterified alkoxylated polyol are preferably selected such that they mimic as closely as possible the analogous properties of the conventional triglyceride being replaced.

Illustrative ingredients (including both fatty food ingredients and non-fat food ingredients) which may be used in combination with the fat mimetics of this invention include carbohydrates (flour, starches, sugars, celluloses), edible lipids (triglycerides), proteins (from animal or vegetable sources), vitamins, (including, but not limited to, fat soluble vitamins such as vitamin A, vitamin D, vitamin E, and vitamin K), antioxidants, emulsifiers (including, but not limited to, the emulsifiers listed as approved for food use in the United States Code of Federal Regulations), thickeners, preservatives, colorants, flavors, fragrances, sugar substitutes (saccharin, aspartame, sucralose, cyclamates, and the like), other fat substitute or fat mimetics (for example, sucrose polyester, esterified propoxylated glycerin having a low proportion (i.e., <10%) of primary ester linkages, or caprenin), bulking agents such as polydextrose, dietary fibers, water, milk, spices, eggs, and the like. Oil-in-water or water-in-oil emulsions can be readily prepared by combining water, the esterified alkoxylated polyol, and other ingredients such as emulsifiers. The esterified alkoxylated polyols of this invention are particularly suitable for the preparation of food compositions requiring exposure to elevated temperatures. Unlike other proposed fat substitutes such as proteinacious macrocolloids or certain polysaccharide-based substances requiring water to render them fat-like in texture, the fat mimetics of this invention are thermally stable and do not readily decompose or lose their fat-like properties, when heated. The fat mimetics thus may readily be utilized in deep fat frying applications to prepare fried foods such as savory snacks, fried chicken, fried fish, french fries, and the like since they will function as effective heat transfer media (that is, they will transmit heat rapidly and uniformly to the food being fried and also provide crisping).

In order to best realize the unique properties and characteristics of the esterified alkoxylated polyols of this invention, such materials are most preferably used as the sole fat substitute in a reduced calorie food product. In particular, the instant esterified alkoxylated polyols are preferably not blended or combined to any substantial extent with esterified alkoxylated polyols having a low proportion of primary ester linkages.

From the foregoing description, one skilled in the art can readily ascertain the essential characteristics of this invention and, various changes and modifications of the invention to adapt it to various usages, conditions, and embodiments.

The following examples further illustrate the compositions of this invention, but are not limitative of the invention in any manner whatsoever.

EXAMPLE 1

Glycerin (43 g) was placed in a nitrogen purged 500 ml round bottom flask. Methylene chloride (50 ml) was then added, followed by boron trifluoride etherate (0.3 ml). The mixture was stirred and cooled in an ice water bath while propylene oxide (216.8 g) was added at a rate so as to maintain the temperature of the mixture between 35° and 40° C. After the addition of 1,2-alkylene oxide was completed, the reaction mixture was stirred for an additional hour before treating with water (1 ml) and CaO (1 g) to neutralize the catalyst. After filtration, the solvent was removed by rotary evaporation to yield a propoxylated glycerin intermediate as a colorless liquid (211.1 g) having the following characteristics:

| | |
|---|---|
| hydroxyl number, mg KOH/g | 308 |
| hydroxyl analysis (NMR) | |
| % primary | 86 |
| % secondary | 14 |
| GPC analysis | |
| Mn | 446 |
| Mw | 496 |
| Mz | 549 |
| polydispersity | 1.1 |
| peak MW | 480 |

The propoxylated glycerin (55.6 g) was combined with a mixture of soybean oil fatty acids (100 g). After heating for 10 hours at 250° C., the esterified propoxylated glycerin was refined by vacuum steam distillation at 250° C. with 2% steam added per hour. After 5 hours, the esterified propoxylated glycerin contained only 0.3% free fatty acids and had a hydroxyl number of 1.8 mg KOH/g (indicating that near-complete esterification was achieved).

The esterified propoxylated glycerin was similar in appearance, odor, and taste to a refined vegetable oil, yet is expected to have a considerably reduced caloric content upon ingestion.

To measure the relative rate of enzyme-catalyzed hydrolysis for the esterified propoxylated glycerin, the composition was challenged by porcine pancreatic lipase. Test emulsions were prepared using the composition according to the procedures described by Naher, "Lipase Titrimetric Assay", in *Methods in Enzymatic Analysis*, Vol. 2, 2nd Eng. ed., p. 814 (1974), except that the composition was not neutralized prior to generation of the emulsion. A 20 mL sample of the composition was utilized. The emulsions were generated in a Waring blender equipped with a stainless steel jacketed container (300 mL capacity). The jacketed blender container was filled with an ice-in-water suspension to cool the emulsion during preparation. Hydrolysis of the composition at pH 8.50 and two enzyme levels (200 and 4000 units/assay) was monitored via the automatic pH star method described by Naber using a Radiometic Copenhagen RTS822 recording titration system (equipped with a PHM84 pH meter and a REA 270 derivatization unit) and a 0.1N sodium hydroxide solution. The enzymatic reaction was maintained at 37° C. under a nitrogen atmosphere.

The results obtained for the esterified alkoxylated polyol obtained as described hereinabove and for olive oil and soybean oil controls are shown in Table I. The table also provides comparative data for a conventional esterified alkoxylated polyol made by reacting 8 equivalents of propylene oxide with one equivalent of glycerin under basic conditions and esterifying with soybean fatty acids; this conventional fat substitute has a low (<5%) proportion of primary ester linkages. The results obtained demonstrate that the composition of this invention is much more resistant towards lipase-catalyzed hydrolysis than olive oil or soybean oil, yet is more susceptible to such cleavage than a conventional esterified alkoxylated polyol prepared in accordance with the teachings of U.S. Pat. No. 4,861,613. This finding was surprising in view of U.S. Pat. Nos. 5,059,443 and 5,077,073, which indicate that the rate of lipase-catalyzed hydrolysis is substantially independent of the structure of the ester linkages in an esterified alkoxylated polyol fat substitute.

TABLE I

| Substrate | Hydrolysis Rate[a] | Hydrolyz-ability[b] | Normalized Hydrolyz-ability[c] |
|---|---|---|---|
| Esterified Propoxylated Glycerin (this invention) | 0.174 | 0.036 | 0.053 |
| Olive Oil | 3.26–7.62 | 1.00 | 1.00 |
| Soybean Oil | 3.62 | 0.738 | 0.723 |
| Esterified Propoxylated Glycerin (Conventional) | — | — | (0.001) |

[a] hydrolysis rate = #μeq/min for an equivalent amount of enzyme
[b] relative to olive oil
[c] normalized hydrolyzability = hydrolyzability compared on an equal m molar basis (taking into account the concentration of ester linkages in a particular sample)

EXAMPLES 2–8

The procedure of Example 1 is repeated using the following fatty acid(s) in place of soybean oil fatty acids.

| Example No. | Fatty Acid |
|---|---|
| 2 | stearic acid |
| 3 | oleic acid |
| 4 | hydrogenated soybean oil fatty acids |
| 5 | corn oil fatty acids |
| 6 | cottonseed oil fatty acids |
| 7 | tallow fatty acids |
| 8 | coconut oil fatty acids |

EXAMPLES 9–12

The procedure of Example 1 is repeated using the following quantities of propylene oxide and the fatty acids indicated.

| Example No | Propylene Oxide, g | Fatty Acid |
|---|---|---|
| 9 | 81.3 | 50 parts peanut oil fatty acids/ 50 parts safflower oil fatty acids |
| 10 | 135.5 | hydrogenated high erucic rapeseed oil fatty acids |
| 11 | 325.2 | behenic acid |
| 12 | 406.5 | lard fatty acids |

EXAMPLES 13–25

The procedure of Example 1 is repeated using the following polyols in place of glycerin and the fatty acids indicated (in sufficient quantity such that at least 20% molar excess is present relative to the hydroxyl number of the propoxylated polyol intermediate).

| Example No. | Polyol | g of Polyol | Fatty Acid |
|---|---|---|---|
| 13 | trimethylolpropane | 62.7 | olive oil fatty acids |
| 14 | sorbitol | 85.1 | canola oil fatty acids |
| 15 | 2,3-butanediol | 42.1 | palm oil fatty acids |
| 16 | 1,6-hexanediol | 55.2 | palm kernel oil fatty acids |
| 17 | tripropylene glycol | 89.7 | fish oil fatty acids |
| 18 | diethylene glycol | 49.5 | lauric acid |
| 19 | propoxylated glycerin[a] | 124.3 | partially hydrogenated soybean oil fatty acids |
| 20 | pentaerythritol | 63.2 | 3 parts behenic acid; 1 part lauric acid |
| 21 | triglycerol | 112.1 | palmitic acid |
| 22 | 2,3,4-pentanetriol | 56.0 | linoleic acid |
| 23 | polytetramethylene glycol[b] | 186.8 | myristic acid |
| 24 | methyl glucoside | 90.8 | 1 part stearic acid; 1 part linolenic acid |
| 25 | propoxylated sucrose[c] | 376.7 | 3 parts behenic acid; 1 part oleic acid; 1 part caprylic acid |

[a] glycerin reacted with 3 equivalents of propylene oxide per equivalent of glycerin under base catalyzed conditions (high secondary hydroxyl content)
[b] average molecular weight = 400
[c] sucrose reacted with 8 equivalents of propylene oxide per equivalent of sucrose as described in U.S. Pat. No. 2,908,681 (Anderson et al.)

EXAMPLE 26

This example demonstrates the use of the esterified alkoxylated polyols of this invention in the preparation of reduced calorie potato chips. A quantity of an esterified propoxylated glycerin obtained in the manner described in Example 1 sufficient to safely fill a 5 pound batch fryer is heated to a temperature of 365° F. (185° C.). Norchip potatoes which have been sliced to a thickness of about 0.052 inches (0.13 c m) are then emerged in the heated esterified propoxylated glycerin for a period of approximately 3 minutes or until the sliced potatoes achieve the desired degree of crispness or moisture content. The potato chips thus produced are then drained and seasoned. As a consequence of utilizing the esterified propoxylated glycerin having a high proportion of primary ester linkages, the available caloric value of the chips is significantly decreased relative to chips cooked in soybean oil, cottonseed oil, or peanut oil.

We claim:

1. An esterified propoxylated glycerin composition suitable for use as a reduced calorie fat substitute wherein
   (a) from 3 to 21 oxypropylene units derived from propylene oxide per equivalent of glycerin attached by ether linkages to glycerin are present;
   from 2 to 3 $C_6$–$C_{24}$ fatty acid acyl groups per equivalent of glycerin attached through ester linkages are present;
   (c) at least 40% of the ester linkages are primary ester linkages; and
   (d) said esterified propoxylated glycerin composition is characterized by the absence of oxyalkylene units derived from ethylene oxide.

2. A fat component useful for preparing a reduced calorie food product, said fat component comprising (a) an edible triglyceride selected from the group consisting of tallow, soybean oil, cottonseed oil, coconut oil, palm kernel oil, corn oil, fish oil, lard, butter fat, olive oil, palm oil, peanut oil, safflower seed oil, cocoa butter, sesame seed oil, rapeseed oil, sunflower seed oil, fully or partially hydrogenated derivatives thereof, and mixtures thereof and (b) the esterified propoxylated glycerin composition of claim 1.

3. A reduced calorie food product comprised of at least one non-fat food ingredient and a fat component, said fat component comprising the esterified propoxylated glycerin composition of claim 1.

4. The esterified propoxylated glycerin composition of claim 1 wherein at least 60% of the ester linkages are primary ester linkages.

5. The esterified propoxylated glycerin composition of claim 1 wherein at least 80% of the ester linkages are primary ester linkages.

6. An esterified propoxylated glycerin composition useful as a reduced calorie fat substitute obtainable by a process comprising
   (a) reacting propylene oxide with glycerin in the absence of ethylene oxide and the presence of an effective amount of a cationic ring-opening polymerization catalyst to form a propoxylated glycerin intermediate wherein at least 40% of the hydroxyl end-groups of said propoxylated glycerin intermediate are primary hydroxyl end-groups and containing from 3 to 21 equivalents of propylene oxide per equivalent of glycerin; and
   (b) reacting the propoxylated glycerin intermediate with a fatty acid entity selected from the group consisting fatty acids, fatty acid anhydrides, fatty acid halides, and alkyl esters of fatty acids to form the esterified propoxylated glycerin composition.

* * * * *